(12) United States Patent
Linford et al.

(10) Patent No.: US 8,202,430 B2
(45) Date of Patent: Jun. 19, 2012

(54) MODIFIED DIAMOND PARTICLE SURFACES AND METHOD

(75) Inventors: Matthew R. Linford, Orem, UT (US); David Scott Jensen, Provo, UT (US); Landon Andrew Wiest, Provo, UT (US)

(73) Assignee: Brigham Young University, Provo, UT (US)

( * ) Notice: Subject to any disclaimer, the term of this patent is extended or adjusted under 35 U.S.C. 154(b) by 426 days.

(21) Appl. No.: 12/557,503

(22) Filed: Sep. 10, 2009

(65) Prior Publication Data
US 2010/0089832 A1 Apr. 15, 2010

Related U.S. Application Data

(60) Provisional application No. 61/191,692, filed on Sep. 10, 2008.

(51) Int. Cl.
*B01D 15/08* (2006.01)
(52) U.S. Cl. .......... 210/656; 210/635; 210/198.2; 210/502.1; 502/439
(58) Field of Classification Search .............. 210/635, 210/656, 659, 198.2, 502.1; 502/439
See application file for complete search history.

(56) References Cited

U.S. PATENT DOCUMENTS

| | | | |
|---|---|---|---|
| 4,298,500 A | 11/1981 | Abbott | |
| 7,326,837 B2 | 2/2008 | Han | |
| 7,427,361 B2 | 9/2008 | Small | |
| 2002/0158022 A1* | 10/2002 | Huang et al. | 210/656 |
| 2004/0118762 A1 | 6/2004 | Xu | |
| 2004/0121070 A1 | 6/2004 | Xu | |
| 2005/0158549 A1 | 7/2005 | Khabashesku | |
| 2005/0189279 A1 | 9/2005 | Xu | |
| 2006/0024434 A1 | 2/2006 | Wang | |
| 2006/0154304 A1 | 7/2006 | Han | |
| 2006/0234269 A1 | 10/2006 | Asplund | |
| 2006/0269467 A1 | 11/2006 | Khabashesku | |
| 2009/0218276 A1 | 9/2009 | Linford | |
| 2010/0089832 A1* | 4/2010 | Linford et al. | 210/656 |

FOREIGN PATENT DOCUMENTS

JP 2004051937 A1 2/2004

OTHER PUBLICATIONS

Bodennec, J. et al., J. Lipid Res. 2000, 41, 1524-1531.
Lee, M. V., et al., Chemistry of Materials, 2007, 19(21), 5052-5054.
Ouyang, T., Journal of Physical Chemistry B 2006, 110, 5611-5620.
Yeap, W. S., Langmuir 2009, 25, 185-191.
Zhong, Y. L., Chem. Mater. 2008, 20, 3137-3144.
Ida, S., Diamond and Related Materials 2003, 12, 601-605.
Tsubota, T., et al., Hyomen Gijutsu 2003, 54, 758.
Kendall, R. A., Computer Phys. Comm. 2000, 128, 260-283.
Bateman, H. G., Food Chem. 1997, 45, 132-134.
Bodennec, J., et al., 2000, 41, 1524-1531.
Akesson-Nilsson, G. J., Chromatogr., A 2003, 996, 173-180.
Ushizawa, K., et al., Chem. Phys. Lett, 2002, 351, 105-108.

(Continued)

*Primary Examiner* — Ernest G Therkorn
(74) *Attorney, Agent, or Firm* — James Sonntag (57) ABSTRACT

A method for preparing modified diamond particles for use in chromatography where hydroxyl groups at the diamond surfaces are reacted with a reactive molecule to introduce a desired functional group at the diamond surface.

29 Claims, 6 Drawing Sheets

OTHER PUBLICATIONS

Harris, J. J., et al., J. Am. Chem. Soc. 1999, 121, 1978-1979.
Zhang, J., P. Biochemistry 2002, 41, 4612-4617.
Yushin, G.N, et al., Effect of Sintering on Structure of Nanodiamond, Science Direct, 2005, 14 pp. 1721-1729 (9 pages).
Hamers, R. J. et al., Diamond and Related Materials 2005, 14, 661-668.
Krysinski. P., et al., J.Am.Chem.Soc. 2003, 125, 12726-12728.
Clare, T. L. et al., Langmiur 2005, 21, 6344-6355.
Yang, W, et al., Langmuir 2004, 20, 6778-6787.
Knickerbocker, T. et al., Langmiur 2003, 19, 1938-1942.
Ando, T.,et al. Diamond and related materials 1996, 5, (10), 1136-1142.
Miller, J.B. et al., Langmiur 1996, 12, 5809-5817.
Liu, Y. et al., Chem. Mater. 2004, 16, 3924-3940, 3924.
Ando. T., et al., Journal of the Chemical Society, Faraday Transactions 1993, 89(11), 1783-1789.
Jiang, T, et al., Journal of the Chemical Society, Faraday Transactions 1996, 92, 3401-3406.
Tse, K.-Y., et al., Journal of Physical Chemistry B 2005, 109, 8523-8532.
Wang, S, et al., J. Phys, Chem. C. 2007, 111, 3986-3995.
Kondo, T. et al., J. Phys. Chem. C. 2007, 111, 12650-12657.
Strother, T. et al., Langmuir 2002, 18,968-971.
Wang, G.T., et al. Journal of the American Chemical Society 2000, 122, 744-745.
Hahn, M.,et al., Journal of Adhesion Science and Technology 2005, 19, 1039-1052.
Scruggs, B. et al., Journal of Physical Chemistry 1993, 97, 9187-9195.
Visbal, H. et al.,Journal of the Ceramic Society of Japan 2004, 112, 95-98.
Notsu, H. et al., Electrochem. Solid-State Lett. 1999, 2 (10) 522-524.
Ohta, R. et al., J. Vac. Sci. Technol. A 2004, 22, 2005-2009.
Nichols, B.M., et al, .Journal of Physical Chemistry B 2005, 109, 20938-20947.
Nakamura, T., et al. Chemical Communications (Cambridge, England) 2003, 7, 900-901.
Lasseter, T., et al., Journal of the American Chemical Society 2004, 126, 10220-10221.
Nakamura, T. et al., Langmuir 2004, 20, 5846-5849.
Tsubota T., et al., Diamond and Related Materials 2002, 11, 1374-1378.
Tsubota T., et al. Physical Chemistry Chemical Physics 2002, 4, 806-811.
Ida, S., et al. Physical Chemistry Chemical Physics 2002, 4, 3881-3886.
Tsubota, T. et al., Physical Chemistry Chemical Physics 2002, 4, 3881-3886.
Ida, S, Langmuir 2003, 19, 9693-9698.
Tsubota, T., et al., Diamond and Related Materials 2004, 13, 1093-1097.
Tsubota, T., et al., Physical Chemistry Chemical Physics 2003, 5, 1474-1480.
Linford, M. R., et al. Journal of the American Chemical Society 1993, 115, 12631-12632.
Linford, M. R., et al., Journal of the American Chemical Society 1995, 117, 3145-3155.
Kim, N. Y., et al. J. Am. Chem. Soc. 1999, 121, 7162.
Vereir, I.E., et al., Appl. Phys. Lett. 1999, 74, 3860.
Fabre, B., et al., Chem. Commun. 2002, 2904-2905.
Fabre, B., et al., J. Phys. Chem. B. 2003, 107, 14326-14335.
Fu, G.D., et al., J. Phys. Chem. B. 2003, 107, 13902-13910.
Cicero, R.L., Langmuir 2002, 18, 305.
Cicero, R.L., Langmuir 2000, 16, 5688-5695.
Tillman, N., et al. J.Am.Chem.Soc. 1988, 110, 6136-6144.
Lee, M V., et al. Chem. Vap. Deposition 2005, 11, 437-443.
Nesterenko, P. N. et al., Analyst 2007, 132, 403-405.
Nesterenko, P. N. et al., Chromatogr., A 2007, 1155, 2-7.
Dyer, M. A., et al., Langmuir 2007, 23, 7018-7023.
Sabu, S. et al. Anal. Biochem. 2007, 367, 190-200.
Chen, W. H., et al., Anal. Chem. 2006, 78, 4228-4234.
Kong, X. L., et al. Anal. Chem. 2005, 77, 4273-4277.
Kaluzny, M. A., et al., J. Lipid 1985, 26, 135-140.

* cited by examiner

ToF-SIMS POS. ION MODE

PIRANHA CLEANED DIAMOND
POSITIVE ION MODE

LiAlH$_4$ TREATED DIAMOND
POSITIVE ION MODE

OCTADECYL ISOCYANTE REACTED DIAMOND
POSITIVE ION MODE

FIG. 2 (cont.)

ToF-SIMS NEG. ION MODE

PIRANHA CLEANED DIAMOND NEGATIVE ION MODE

LiAlH$_4$ TREATED DIAMOND NEGATIVE ION MODE

OCTADECYL ISOCYANTE REACTED DIAMOND NEGATIVE ION MODE

MODIFIED DIAMOND PARTICLE SURFACES AND METHOD

CROSS REFERENCE TO RELATED APPLICATIONS

Priority is claimed from U.S. Provisional Patent Application 61/191,692, filed 10 Sep. 2008, which is hereby incorporated by reference.

BACKGROUND

Since the inception of modern chromatography, silica based stationary phases have dominated the world of chemical separations. Unfortunately, silica has certain limitations. Under acidic conditions, silica tends to lose its functionality and under basic conditions it dissolves entirely after a matter of hours. Not until recently have alternatives to silica been available such as polymer based stationary phases. These tend to swell when exposed to organic solvents and are therefore not ideal for reversed-phase separations.

Chemists have worked around the limitations of available stationary phases, but these workarounds often result in less than ideal outcomes. For instance, certain separations may need to occur under basic or acidic conditions because the analyte of interest may only be stable under a certain pH range. It is would therefore be ideal to find a phase that could perform a separation under extreme pHs that current phases cannot successfully do separations at.

Diamond has usually been assumed to be inert and relatively little has been done to investigate the possibility of diamond as the basis for a stationary phase. Nosterenko et al. has performed separations of proteins using oxidized/cleaned diamond and Saini et al. has been successful in coating the diamond surface with poly(allylamine). This coated diamond was then used as a normal phase in Solid-phase Extraction (SPE). Saini's study also showed that his phase was extremely stable under extreme pH conditions (from pH 0-pH 14) for 24 h. The SPE column was able to be reused many times and showed no signs of degradation. It also performed in the same manner experiment after experiment and only required a flush with ethyl acetate in between uses.

These two groups have shown that separations can indeed be performed with diamond as the basis for a stationary phase. Nesterenko's study lacked good resolution in it HPLC spectra and Saini's capacity was quite low, but efforts are being made to remedy the capacity issue.

CITED REFERENCES

SUMMARY

Figure 1:
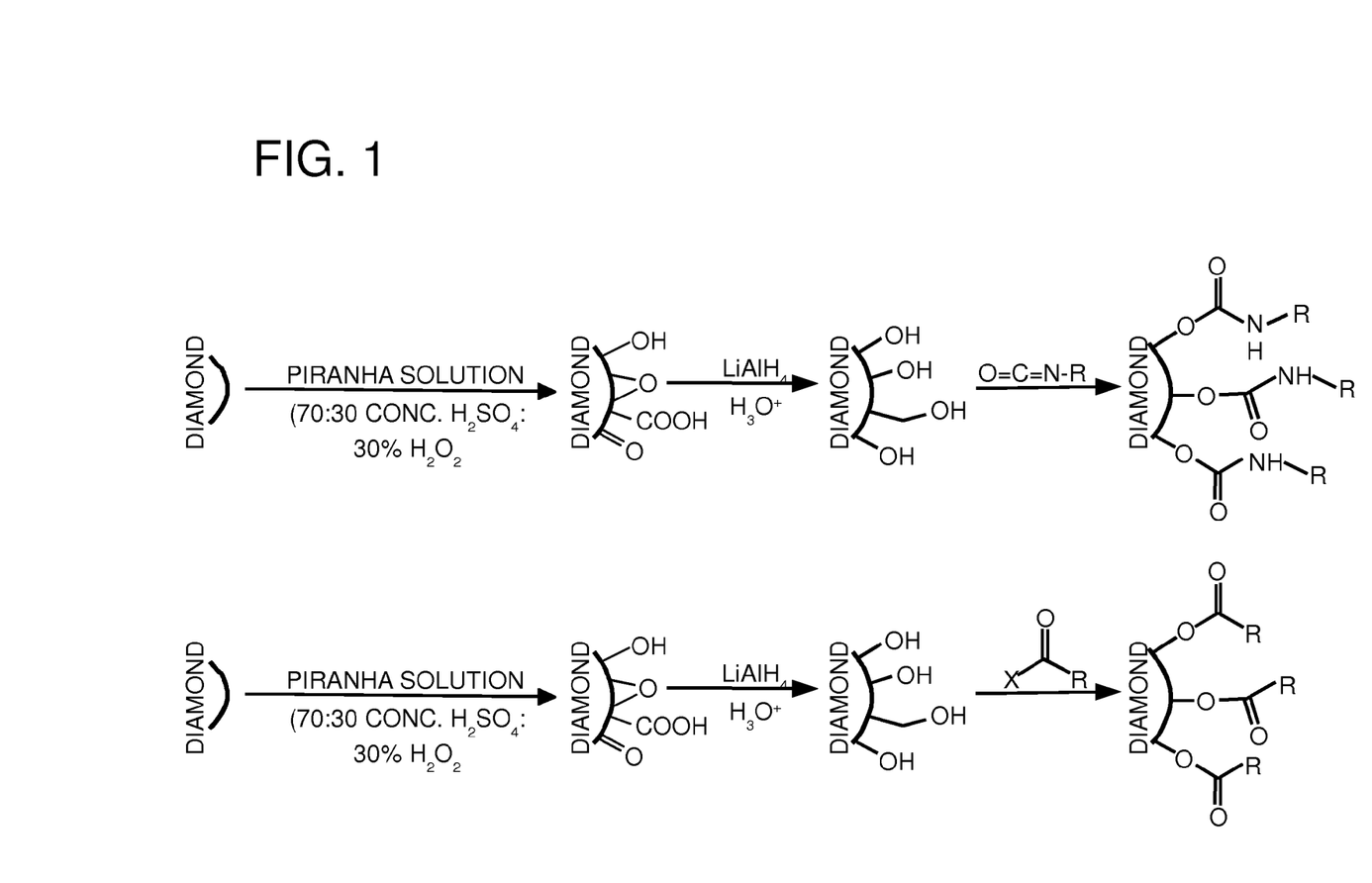
FIG. 1: Scheme outlining basic chemistry for the formation of the isocyanate and acyl halide reacted diamond particles

A new phase is directly bonded to the diamond surface which has been largely hydroxyl terminated. In a specific example, diamond cleaned with piranha solution is treated with lithium aluminum hydride (LAH). This reaction greatly increases the amount of hydroxyl groups on the diamond surface. Since hydroxyl groups are reactive to various functional groups, this chemistry is exploited to attach ligands directly to the diamond surface. For example, isocyanates and acyl halides (primarily Br and Cl) are reactive to the hydroxyl functional group and form urethane and ester linkages respectively, that are directly bonded to the diamond surface. (See FIG. 1)

Bases do have the ability to hydrolyze this linkage at the carbonyl site, so bulky groups (methyl, isopropyl, tert-butyl, phenyl etc.) can be attached to the α-carbon of the ligand to sterically hinder the binding site and prevent bases from accessing the partially negative carbon. This should give this type of linkage greater stability in the presence of acids and bases. The reusability and consistency of the column is also expected to be similar to that of Saini's column and this chemistry can be applied to HPLC and SPE stationary phases.

An aspect is a method for preparing modified diamond particles for use in chromatography where hydroxyl groups at the diamond surfaces are reacted with a reactive molecule to introduce a desired functional group at the diamond surface. An example is the reaction of Isocyanates and acyl halides with hydroxyl-terminated diamond to form HPLC/SPE stationary phases.

Another aspect is a method for preparing modified diamond particles for use in chromatography where i) diamond particles are reacted with an oxidizing agent that introduces carboxyl groups at the surface of the diamond, ii) the carboxyl groups are reduced to primary alcohols, and iii) the primary alcohols are reacted with a reactive molecule to introduce a desired functional group at the diamond surface.

The diamond particles of the present method can by used in any suitable type of chromatography type. These include, for example, high performance liquid chromatography (HPLC), ultra performance liquid chromatography (HPLC), solid phase extraction, electrochromatography, size-exclusion chromatography, ion chromatography, affinity chromatography.

The chromatography may be practiced at any suitable pressure, such as for example, between 1000 psi and 15000 psi.

The diamond surface may be prepared by reducing the surface with a suitable reducing agent prior to reaction with the reactive molecule. Any suitable reducing agent is contemplated, such as, for example, lithium aluminum hydride.

The reactive function group may be any suitable functional group with the desired reactivity, and may have attached to the reactive group an alkyl group or aryl group. The alkyl group may have the form $-(CH_2)_n CH_3$, where n=0-25. The alkyl group may be branched or unbranched. The alkyl group may be partially or fully fluorinated, The aryl group may have the form $-C_6H_6$. The aryl group may be partially or fully fluorinated.

Examples of the reactive functional groups include, one of or a mixture of an alkyl isocyanate, an aryl isocyanate, an acid chloride with an aromatic group, an acid chloride with an alkyl group, an acid bromide, an alkyl halide, an aryl halide, a benzyl halide, a benzyl triflate, a benzyl mesylate, an alkyl mesylate, an alkyl tosylate, and an alkyl triflate.

The reactive functional group may contain more than one other group near the reactive site of the molecule, which provides steric hindrance for the adsorbed species.

The reactive molecule may contain C—H bonds. The reactive molecule may contain an electrophilic site and a leaving group.

Another aspect is a diamond particle for use in chromatography containing groups tethered to the diamond surface through ether, ester, or urethane linkages.

DETAILED DESCRIPTION

Example

Experimental

Micro-diamond or diamond powder is treated with piranha solution (3:7 30% $H_2O_2$:conc. $H_2O_2$:conc. $H_2SO_4$) or any other suitable cleaning/etching solution. This cleans/etches the diamond surface and exposes the various functional groups that naturally occur on the diamond surface. The diamond must be dried thoroughly before the next step. This can be performed by pulling argon through the powder or placing the powder in a vacuum for many hours. The dryness can be verified by diffuse reflectance infrared Fourier transform (DRIFT).

The cleaned dry diamond is then treated with 1M $LiAlH_4$ (LAH) suspended in THF (or any other strongly reducing base) [1] for 24-68 h at room temperature (about 1 g diamond:5 mL LAH solution). Warning: LAH is extremely reactive to water. Use proper PPE. The reaction must be performed under inert atmosphere (argon) and all glassware must be dry. The reaction is quenched by 1M HCl. This should be added very slowly due to the reactivity of LAH with water and HCl. Once the reaction is quenched, the diamond is filtered over a fine fritted Buchner funnel and washed with copious amounts of water. If white particles are present, rinse with more 1 M HCl to dissolved the reacted LAH. Once thoroughly rinsed, the powder is dried completely. This gives hydroxyl terminated diamond.

The reduced surface has been disclosed US patent [1], the reaction of the hydroxylated surface with various functional groups is not disclosed. The present method is an improvement over the disclosed diamond-based chromatographic processes.

Another US patent [2] discloses powders "attached with hydrocarbon, amino, carboxylic acid, or sulfonic acid groups." The present method is specifically targeting the reaction of the hydroxylated surface with a reactive molecule to introduce a desired functional group at the diamond surface, such as, for example, reactive isocyanates and acyl halides, and this chemistry and these functional groups are not disclosed.

In a specific example, for this final step the hydroxyl terminated diamond is then placed in a reaction vessel which is subsequently flushed with inert atmosphere. Then a reactive molecule is added to the powder. For example, a desired isocyanate or acyl halide is added to the powder (about 0.5 mL:1 g hydroxyl terminated diamond) then add enough dry tetrahydrofuran (THF) or ether to completely dissolve the isocyanate or acyl halide. The reaction should then react for at least 18 h at room temperature. Filter the diamond over a fine fritted Buchner funnel and wash with a large amount of THF or ether to rinse away the unreacted isocyanate or acyl halide. Dry the powder completely. The powder is then suspended in a solvent and pressed into an HPLC column.

Results and Discussion

Thus far, only octadecyl isocyanate has been reacted with the hydroxyl terminated diamond. The evidence of the successive reactions can be seen in FIG. 2 by the DRIFT, ToF-SIMS and XPS spectra. There is a decrease in the height of the alcohol peak (~3500 $cm^{-1}$) seen in the octadecyl isocyanate DRIFT spectrum as compared to the LAH spectrum. It is clear that not all of the alcohol functional groups are reacted and this is attributed to the steric hindrance of the diamond surface. The 2° amine peak at 3342.43 $cm^{-1}$, asymmetric and symmetric C—H stretches at 2920.95 $cm^{-1}$ and 2848.21 $cm^{-1}$ and the carbonyl stretches at 1612.33 $cm^{-1}$ and 1572.64 $cm^{-1}$ are indicative of successful bonding of octadecyl isocyanate to the hydroxyl terminated surface as evidenced by the urethane (carbamide) linkage.

Figure 2:
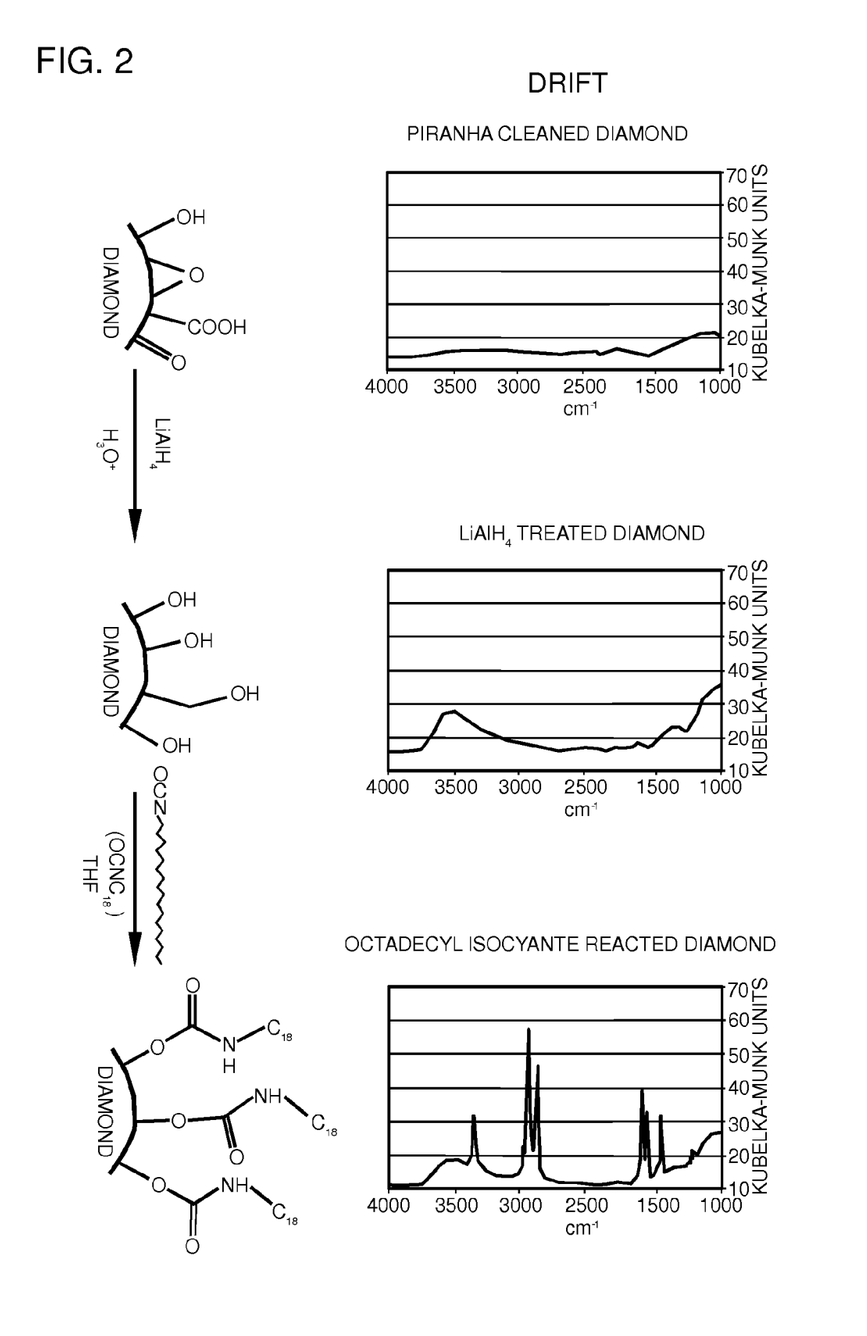
FIG. 2: Spectra confirming the step by step synthesis of a carbamide linked $C_{18}$ chain to the diamond surface

The ToF-SIMS data shows an increase of hydrocarbon fragments in the positive ion spectra and a decrease of O (16 m/z) and OH (17 m/z) fragments in the negative ion spectra. This result is predicted because fewer O and OH groups would be exposed on the diamond surface once the isocyanate group has reacted with the OH functional group. The XPS spectrum shows the presence of nitrogen which is absent from the piranha and LAH treated diamond powders. The only source of nitrogen in this experiment is from the isocyanate group. This therefore further confirms the formation of the carbamide linkage on the diamond surface.

In another embodiment, an HPLC column is packed with 5 μm octadecyl isocyanate reacted diamond powder. If nonporous diamond is used, few plates are expected to be present on the column. This should be remedied by using porous diamond powder.

Figure 3:
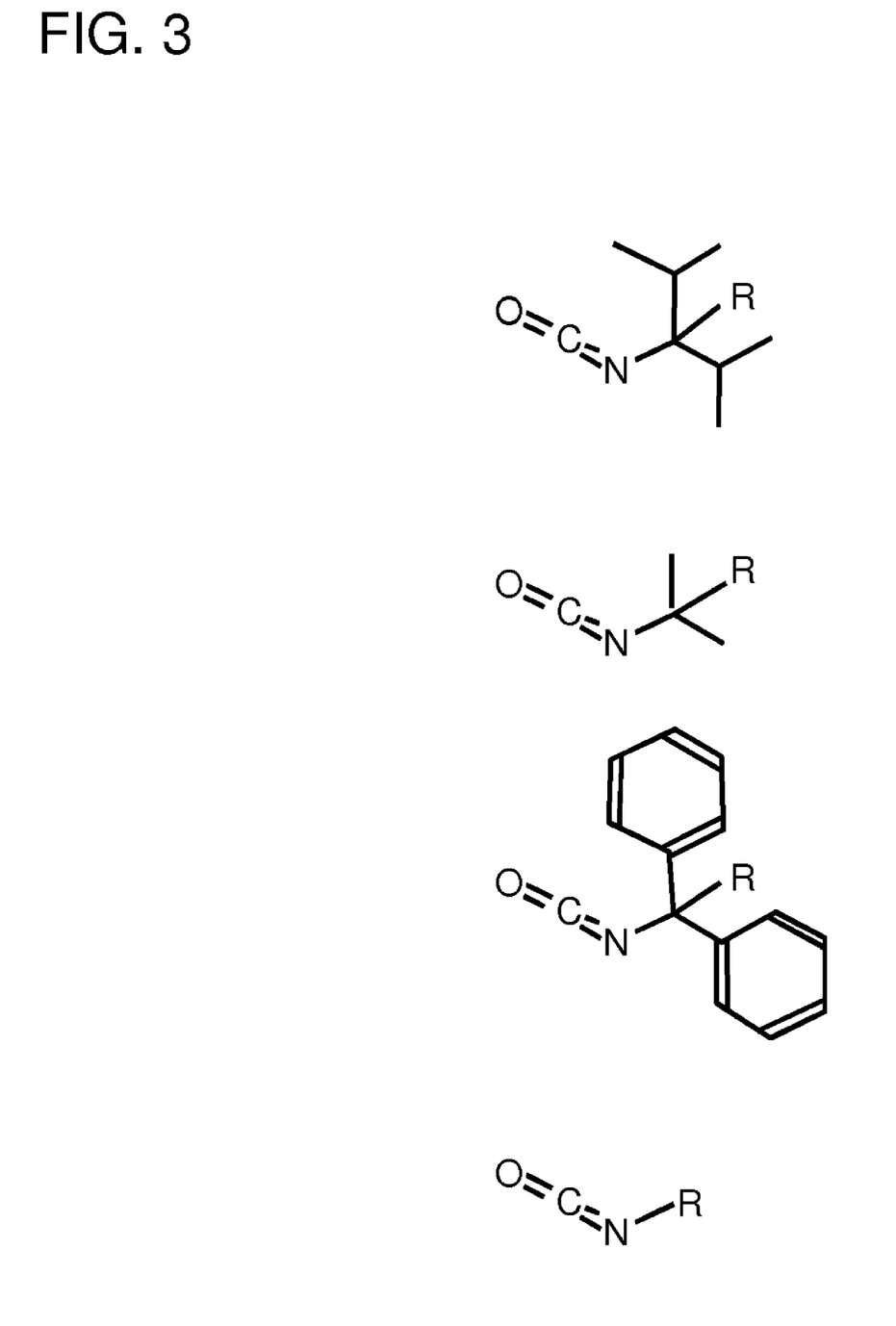
FIG. 3: Possible examples of the types of groups attached at the α-carbon site to increase sterics of the area in order to prevent nucleophilic attack of a base at the carbonyl resulting in hydrolysis of the ether or urethane linkage.

The chemistry of the present method is expected to work with various isocyanates and acyl halides, including compounds with the disubstituted α-carbons (see FIG. 3 for some examples). The acyl halide derivatives of these compounds would also be used including the tert-butyl group not shown in the figure. Other functional groups past the functionalized α-carbon could include but are not limited to phenyl, naphthyl, chiral, perfluorinated, $C_8$, and $C_{10}$.

CONCLUSION

The chemistry for creating urethane (carbamide) linkages to the diamond surface is straight forward and should prove useful in the creation of diamond-based HPLC and SPE stationary phases. The attachment of octadecyl isocyanate to the diamond surface has been verified and other isocyanates/acyl halides should also react in a similar manner to the hydroxyl terminated diamond surface.

Once a diamond-based HPLC column is successfully created and used, the added stability, reusability and consistency of these diamond columns will exceed that of its similarly functionalized silica-based counterparts. This strength comes from the urethane and/or ester linkages which bind the diamond and the functional group together. This will result in greater stability at more extreme pHs and the disubstituted α-carbon should help increase the stability further in basic conditions.

While invention has been described with reference to certain specific embodiments and examples, it will be recognized by those skilled in the art that many variations are possible without departing from its scope and spirit, and that any invention, as described by the claims, is intended to cover all changes and modifications that do not depart from the spirit of the invention.

What is claimed is:

1. A method for preparing modified diamond particles for use in chromatography comprising reacting hydroxyl groups at the diamond surfaces with a reactive molecule to introduce a desired functional group at the diamond surface.

2. A method for preparing modified diamond particles for use in chromatography comprising reacting hydroxyl groups at the diamond surfaces with a reactive molecule to introduce a desired functional group at the diamond surface, the reactive functional group being one or more of an alkyl isocyanate, aryl isocyanate, an acid chloride with an aromatic group, an acid chloride with an alkyl group, acid bromide, alkyl halide, aryl halide, benzyl halide, benzyl triflate, benzyl mesylate, alkyl mesylate, alkyl tosylate, and alkyl triflate.

3. A method for preparing modified diamond particles for use in chromatography comprising reacting hydroxyl groups at the diamond surfaces with a reactive molecule to introduce a desired reactive functional group at the diamond surface,
the reactive functional group, in addition to a reactive site, having one of or more from alkyl groups, and aryl groups.

4. The method of claim 3 wherein the alkyl group is —(CH2)$_n$CH3, where n=0-25.

5. The method of claim 3 wherein the alkyl group is branched.

6. The method of claim 3 wherein the alkyl group is partially or fully fluorinated.

7. The method of claim 3 wherein the aryl group is —$C_6H_5$.

8. The method of claim 3 wherein the aryl group is partially or fully fluorinated.

9. The method of claim 3 in which the reactive functional group comprises one or more of alkyl isocyanate, aryl isocyanate, acid chloride with an aromatic group, acid chloride with an alkyl group, acid bromide, alkyl halide, aryl halide, benzyl halide, benzyl triflate, benzyl mesylate, alkyl mesylate, alkyl tosylate, and alkyl triflate.

10. A method for preparing modified diamond particles for use in chromatography comprising reacting hydroxyl groups at the diamond surfaces with a reactive molecule to introduce a desired reactive functional group at the diamond surface,
the reactive functional group, in addition to a reactive site, having one or both of an alkyl group, and an aryl group, wherein the reactive functional group has more than one other group near the reactive site of the molecule, which provides steric hindrance for adsorbed species.

11. A method for preparing modified diamond particles for use in chromatography comprising reacting hydroxyl groups at the diamond surfaces with a reactive molecule to introduce a desired functional group at the diamond surface,
the reactive functional group being one or more of alkyl isocyanate, aryl isocyanate, acid chloride with an aromatic group, acid chloride with an alkyl group, acid bromide, alkyl halide, aryl halide, benzyl halide, benzyl triflate, benzyl mesylate, alkyl mesylate, alkyl tosylate, and alkyl triflate.

12. A method for preparing modified diamond particles for use in chromatography comprising i) reacting diamond particles with an oxidizing agent that introduces carboxyl groups at the surface of the diamond, ii) reducing said carboxyl groups to primary alcohols, and iii) reacting the primary alcohols with a reactive molecule to introduce a desired functional group at the diamond surface.

13. The method of claim 12 additionally comprising conducting a chromatography process with the diamond particles, where the chromatography process is high performance liquid chromatography (HPLC), ultra performance liquid chromatography (HPLC), solid phase extraction chromatography, electrochromatography, size-exclusion chromatography, ion chromatography, or affinity chromatography.

14. The method of claim 13 in which the chromatography process is practiced at a pressure of between 1000 psi and 15,000 psi.

15. The method of claim 12 in which the diamond surface is reduced with a reducing agent prior to reacting with the reactive molecule.

16. The method of claim 15 in which the reducing agent is lithium aluminum hydride.

17. The method of claim 12 in which the reactive molecule contains C—H bonds.

18. The method of claim 12 in which the reactive molecule contains an electrophilic site and a leaving group.

19. A method for preparing modified diamond particles for use in chromatography comprising i) reacting diamond particles with an oxidizing agent that introduces carboxyl groups at the surface of the diamond, ii) reducing said carboxyl groups to primary alcohols, and iii) reacting the primary alcohols with a reactive molecule to introduce a desired reactive functional group at the diamond surface;
the reactive functional group, in addition to a reactive site, having one or both of an alkyl group, and an aryl group.

20. The method of claim 19 wherein the alkyl group is —$(CH_2)_n CH_3$, where n=0-25.

21. The method of claim 19 wherein the alkyl group is branched.

22. The method of claim 19 wherein the alkyl group is partially or fully fluorinated.

23. The method of claim 19 wherein the aryl group is —$C_6H_5$.

24. The method of claim 19 wherein the aryl group is partially or fully fluorinated.

25. The method of claim 19 wherein the reactive functional group has more than one other group near the reactive site of the molecule, which provides steric hindrance for adsorbed species.

26. The method of claim 19 in which the reactive functional group comprises one or more of alkyl isocyanate, aryl isocyanate, acid chloride with aromatic group, acid chloride with an alkyl group, acid bromide, alkyl halide, aryl halide, benzyl halide, benzyl triflate, benzyl mesylate, alkyl mesylate, alkyl tosylate, and alkyl triflate.

27. A method for preparing modified diamond particles for use in chromatography comprising;
i) reacting diamond particles with an oxidizing agent that introduces carboxyl groups at the surface of the diamond,
ii) reducing said carboxyl groups to primary alcohols, and
iii) reacting the primary alcohols with a reactive molecule to introduce a desired reactive functional group at the diamond surface;
the reactive functional group one or more of an alkyl isocyanate, aryl isocyanate, an acid chloride with an aromatic group, an acid chloride with an alkyl group, acid bromide, alkyl halide, aryl halide, benzyl halide, benzyl triflate, benzyl mesylate, alkyl mesylate, alkyl tosylate, and alkyl triflate.

28. A method for preparing modified diamond particles for use in chromatography comprising;
treating diamond particle surfaces to produce hydroxyl groups on the surface,
treating the surfaces having hydroxyl groups with isocyanate or acyl halide to produce reactive functional groups on the surfaces.

29. A method for preparing modified diamond particles for use in chromatography comprising;
treating diamond particle surfaces to produce hydroxyl groups on the surface,
treating the surfaces having hydroxyl groups with isocyanate or acyl halide to produce reactive functional groups on the surfaces;
reactive functional groups having more than one other group near the reactive site of the molecule, which provides steric hindrance for adsorbed species.

* * * * *